US00PP22645P2

(12) United States Plant Patent
Dümmen

(10) Patent No.: US PP22,645 P2
(45) Date of Patent: Apr. 10, 2012

(54) ***OSTEOSPERMUM* PLANT NAMED 'DUETISWIPU'**

(50) Latin Name: *Osteospermum ecklonis*
Varietal Denomination: Duetiswipu

(75) Inventor: Tobias Dümmen, Rheinberg (DE)

(73) Assignee: Capital Green Investments Ltd., Grand Cayman (KY)

( * ) Notice: Subject to any disclaimer, the term of this patent is extended or adjusted under 35 U.S.C. 154(b) by 0 days.

(21) Appl. No.: 12/924,015

(22) Filed: Sep. 17, 2010

(51) Int. Cl.
*A01H 5/00* (2006.01)

(52) U.S. Cl. ..... Plt./360

(58) Field of Classification Search ..... Plt./360
See application file for complete search history.

*Primary Examiner* — Susan McCormick Ewoldt
(74) *Attorney, Agent, or Firm* — C. A. Whealy

(57) ABSTRACT

A new and distinct cultivar of *Osteospermum* plant named 'Duetiswipu', characterized by its compact, outwardly spreading and mounded plant habit; freely branching growth habit; early and freely flowering habit; and daisy-type inflorescences with elongated oblong-shaped ray florets that are dark purple violet in color.

1 Drawing Sheet

Botanical designation: *Osteospermum ecklonis*.
Cultivar denomination: 'DUETISWIPU'.

CROSS-REFERENCED TO CLOSELY-RELATED APPLICATIONS

Title: *Osteospermum* Plant Named 'Duetiswila'
Applicant: Tobias Dümmen
Filed: Concurrently with this application Ser. No. 12/924,014

BACKGROUND OF THE INVENTION

The present invention relates to a new and distinct cultivar of *Osteospermum* plant, botanically known as *Osteospermum ecklonis* and hereinafter referred to by the name 'Duetiswipu'.

The new *Osteospermum* plant is a product of a planned breeding program conducted by the Inventor in Rheinberg, Germany. The objective of the program is to create and develop new compact and freely branching *Osteospermum* plants with an outwardly spreading plant habit and numerous attractive inflorescences.

The new *Osteospermum* plant originated from a cross-pollination conducted by the Inventor in August, 2007 of a proprietary selection of *Osteospermum ecklonis* identified as code number Q06-6099-501, not patented, as the female, or seed, parent with a proprietary selection of *Osteospermum ecklonis* identified as code number F616-1618, not patented, as the male, or pollen, parent. The new *Osteospermum* plant was discovered and selected by the Inventor as a single flowering plant from within the progeny of the stated cross-pollination in a controlled greenhouse environment in Rheinberg, Germany in May, 2009.

Asexual reproduction of the new *Osteospermum* plant by terminal cuttings in a controlled environment in Rheinberg, Germany since May, 2009, has shown that the unique features of this new *Osteospermum* plant are stable and reproduced true to type in successive generations.

SUMMARY OF THE INVENTION

Plants of the new *Osteospermum* have not been observed under all possible environmental conditions. The phenotype may vary somewhat with variations in environment such as temperature and light intensity, without, however, any variance in genotype.

The following traits have been repeatedly observed and are determined to be the unique characteristics of 'Duetiswipu'. These characteristics in combination distinguish 'Duetiswipu' as a new and distinct cultivar of *Osteospermum* plant:

1. Compact, outwardly spreading and mounded plant habit.
2. Freely branching growth habit.
3. Early and freely flowering habit.
4. Daisy-type inflorescences with elongated oblong-shaped ray florets that are dark purple violet in color.

In side-by-side comparisons conducted in Rheinberg, Germany, plants of the new *Osteospermum* differ primarily from plants of the female parent selection in ray floret color as plants of the female parent selection have white-colored ray florets. In addition, plants of the new *Osteospermum* are more compact than plants of the female parent selection.

In side-by-side comparisons conducted in Rheinberg, Germany, plants of the new *Osteospermum* differ primarily from plants of the male parent selection in ray floret color as plants of the male parent selection have purple-colored ray florets. In addition, plants of the new *Osteospermum* are more outwardly spreading than and not as upright as plants of the male parent selection.

Plants of the new *Osteospermum* can be compared to plants of *Osteospermum ecklonis* 'Duetiswila', disclosed in a U.S. Plant Patent application filed concurrently. In side-by-side comparisons, plants of the new *Osteospermum* differ primarily from plants of 'Duetiswila' in ray floret color as plants of the new *Osteospermum* have darker colored ray florets. In addition, plants of the new *Osteospermum* are smaller than plants of 'Duetiswila'.

Plants of the new *Osteospermum* can be compared to plants of the *Osteospermum ecklonis* 'Sunbrella Purple', not patented. In side-by-side comparisons conducted in Rheinberg, Germany, plants of the new *Osteospermum* differed primarily from plants of 'Sunbrella Purple' in the following characteristics:

1. Plants of the new *Osteospermum* were more outwardly spreading than plants of 'Sunbrella Purple'.

2. Plants of the new *Osteospermum* had thicker stems than plants of 'Sunbrella Purple'.
3. Plants of the new *Osteospermum* had larger leaves than plants of 'Sunbrella Purple'.
4. Ray florets of plants of the new *Osteospermum* were slightly darker in color than ray florets of plants of 'Sunbrella Purple'.

BRIEF DESCRIPTION OF THE PHOTOGRAPH

The accompanying photograph illustrates the overall appearance of the new *Osteospermum* plant showing the colors as true as it is reasonably possible to obtain in colored reproductions of this type. Colors in the photograph may differ slightly from the color values cited in the detailed botanical description which accurately describe the colors of the new *Osteospermum* plant. The photograph comprises a side perspective view of a typical flowering plant of 'Duetiswipu' grown in a container.

DETAILED BOTANICAL DESCRIPTION

The aforementioned photograph, following observations and measurements describe plants grown during the spring and summer in 10.5-cm containers in a glass-covered greenhouse in Rheinberg, Germany and under conditions and practices which approximate those generally used in commercial *Osteospermum* production. During the production of the plants, day and night temperatures averaged 18° C. and light levels averaged 4,500 lux. Measurements and numerical values represent averages for typical flowering plants. Plants were pinched three weeks after planting and were 13 weeks old when the photograph and description were taken. In the following description, color references are made to The Royal Horticultural Society Colour Chart, 2001 Edition, except where general terms of ordinary dictionary significance are used.

Botanical classification: *Osteospermum ecklonis* 'Duetiswipu'.

Parentage:

*Female, or seed, parent.*—Proprietary selection of *Osteospermum ecklonis* identified as code number Q06-6099-501, not patented.

*Male, or pollen, parent.*—Proprietary selection of *Osteospermum ecklonis*, identified as code number F616-1618, not patented.

Propagation:

*Type.*—Terminal vegetative cuttings.

*Time to initiate roots, summer.*—About five days at 20° C.

*Time to initiate roots, winter.*—About seven days at 20° C.

*Time to produce a rooted young plant, summer.*—About three weeks at 20° C.

*Time to produce a rooted young plant, winter.*—About four weeks at 20° C.

*Root description.*—Fine, fibrous; white in color.

*Rooting habit.*—Freely branching; dense.

Plant description:

*Plant form and growth habit.*—Compact, outwardly spreading and mounded plant habit; inflorescences positioned above the foliar plane; moderately vigorous growth habit.

*Plant height.*—About 17 cm.

*Plant diameter.*—About 23 cm.

*Lateral branches.*—Quantity per plant: Freely branching habit, about six lateral branches develop per plant. Length: About 15 cm. Diameter: About 4 mm. Internode length: About 1 cm. Strength: Strong. Texture: Smooth, glabrous. Color: Close to 144B.

*Foliage description.*—Arrangement: Alternate, simple. Length: About 5.8 cm. Width: About 1.7 cm. Shape: Spatulate. Apex: Acute. Base: Attenuate. Margin: Dentate. Texture, upper surface: Pubescent; leathery. Texture, lower surface: Smooth, glabrous; leathery. Venation pattern: Pinnate. Color: Developing leaves, upper surface: Close to 137B. Developing leaves, lower surface: Close to 144A. Fully expanded leaves, upper surface: Close to 137A; venation, close to 144B. Fully expanded leaves, lower surface: Close to 137B to 137C; venation, close to 144B. Petiole length: About 1 cm. Petiole diameter: About 4.2 mm. Petiole texture, upper and lower surfaces: Smooth, glabrous. Petiole color, upper surface: Close to 144A to 144B. Petiole color, lower surface: Close to 144B.

Inflorescence description:

*Appearance/habit.*—Daisy-type inflorescence form with elongated oblong-shaped ray florets; inflorescences positioned above the foliar plane; disc and ray florets developing acropetally on a capitulum; inflorescences face mostly upright to somewhat outwardly; freely flowering habit; about 35 inflorescences develop per plant.

*Fragrance.*—None detected.

*Natural flowering season and flowering response.*—In Germany, plants of the new *Osteospermum* flower continuously during the spring and summer; early flowering habit, plants begin flowering about six weeks after planting.

*Flower longevity.*—Inflorescences last about three days on the plant; inflorescences not persistent.

*Inflorescence bud.*—Height: About 1.2 cm. Diameter: About 8.5 mm. Shape: Ovate. Color: Close to 137B and 144C.

*Inflorescence size.*—Diameter: About 5.5 cm. Depth (height): About 2.5 cm. Disc diameter: About 8 mm. Receptacle diameter: About 3 mm. Receptacle height: About 3 mm.

*Ray florets.*—Shape: Elongated oblong. Length: About 3 cm. Width: About 6.8 mm. Apex: Emarginate. Base: Obtuse. Margin: Entire. Texture: Smooth, glabrous. Number of ray florets per inflorescence: About 16 to 22 arranged in about two whorls. Color: When opening, upper surface: Close to 82A. When opening, lower surface: Close to 89C. Fully opened, upper surface: Close to 81A; color becoming closer to 89C with development. Fully opened, lower surface: Close to 78C and 83B.

*Disc florets.*—Shape: Tubular; apex dentate, five-pointed. Length: About 5 mm. Diameter, apex: About 2 mm. Diameter, base: About 1 mm. Number of disc florets per inflorescence: About 50. Color: Immature: Close to 93C. Mature: Close to 93A to 93C.

*Phyllaries.*—Quantity per inflorescence: About 16 to 22. Length: About 6.8 mm. Width: About 4.6 mm. Shape: Lanceolate. Apex: Apiculate. Base: Acute. Margin: Entire. Texture, upper and lower surfaces: Smooth, glabrous; leathery. Color, upper surface: Close to 137B to 137C. Color, lower surface: Close to 137C.

*Peduncles.*—Length: About 10 cm. Diameter: About 2 mm. Strength: Strong. Aspect: Mostly upright. Texture: Smooth, glabrous; leathery. Color: Close to 144A.

*Reproductive organs.*—Androecium: Present on disc florets only. Anther shape: Ovate. Anther length: About 2 mm. Anther color: Close to 79A to 79B. Pollen amount: Abundant. Pollen color: Close to 23A. Gynoecium: Present on both ray and disc florets. Pistil length: About 7 mm. Stigma shape: Crested. Stigma color: Close to 79A. Style length: About 3 mm. Style color: Close to 79A. Ovary color: Close to 144C.

*Seeds.*—Length: About 7 mm. Diameter: About 3 mm. Color: Close to 199A.

Disease/pest resistance: Plants of the new *Osteospermum* have not been shown to be resistant to pathogens and pests common to *Osteospermums.*

Temperature tolerance: Plants of the new *Osteospermum* have been observed to tolerate temperatures ranging from about 5° C. to about 35° C.

It is claimed:

1. A new and distinct *Osteospermum* plant named 'Duetiswipu' as illustrated and described.

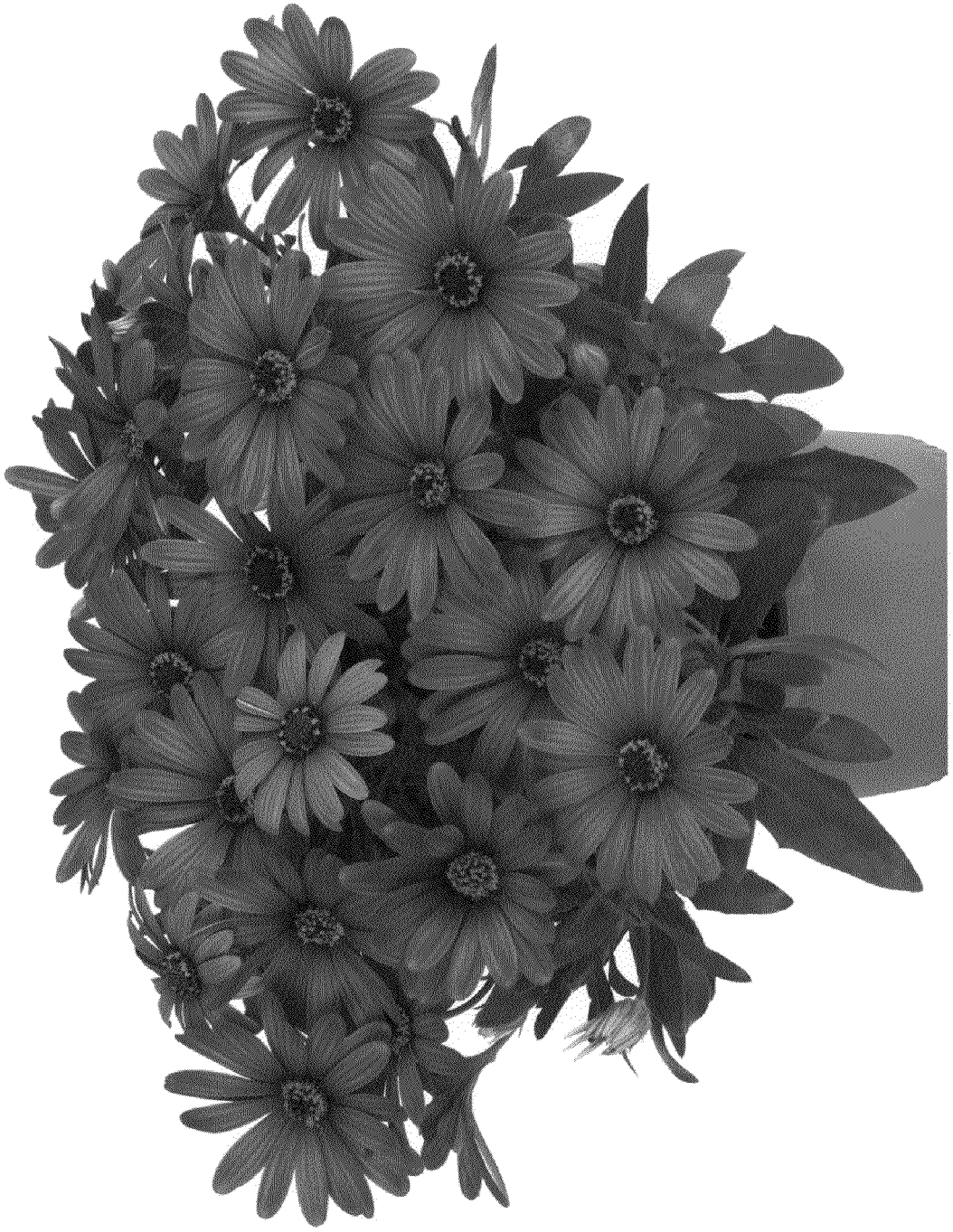

* * * * *